(12) United States Patent
Gilson

(10) Patent No.: US 6,514,280 B1
(45) Date of Patent: Feb. 4, 2003

(54) DELIVERY CATHETER

(75) Inventor: Paul Gilson, Moycullen (IE)

(73) Assignee: Salviac Limited, Dublin (IE)

( * ) Notice: Subject to any disclaimer, the term of this patent is extended or adjusted under 35 U.S.C. 154(b) by 0 days.

(21) Appl. No.: 09/676,085

(22) Filed: Oct. 2, 2000

Related U.S. Application Data

(63) Continuation of application No. PCT/IE99/00020, filed on Apr. 1, 1999.

(30) Foreign Application Priority Data

Apr. 2, 1998 (IE) ................................................. 980241

(51) Int. Cl.⁷ ................................................. A61F 2/06
(52) U.S. Cl. ................................................. 623/1.11
(58) Field of Search ..................... 623/1.11, 1.12, 623/1.22; 606/108, 191, 194, 195, 198, 200

(56) References Cited

U.S. PATENT DOCUMENTS

| | | | |
|---|---|---|---|
| 5,026,377 A | | 6/1991 | Burton et al. |
| 5,531,719 A | * | 7/1996 | Takahashi .................. 604/280 |
| 5,609,608 A | * | 3/1997 | Benett et al. ............... 606/205 |
| 5,683,451 A | * | 11/1997 | Lenker et al. ................ 623/1 |
| 5,885,258 A | * | 3/1999 | Sachdeva et al. ........... 604/281 |
| 5,895,410 A | * | 4/1999 | Forber et al. ............... 606/200 |

FOREIGN PATENT DOCUMENTS

| | | |
|---|---|---|
| EP | 0 696 447 A2 | 2/1996 |
| WO | WO 97/41778 | 11/1997 |
| WO | WO 98/06355 | 2/1998 |
| WO | WO 98/14224 | 4/1998 |

* cited by examiner

Primary Examiner—Michael J. Milano
Assistant Examiner—Vy Q. Bui
(74) Attorney, Agent, or Firm—Finnegan, Henderson, Farabow, Garrett & Dunner, LLP

(57) ABSTRACT

A catheter for transvascular deployment of a radially compressible medical device has a tubular outer body within which is slidably mounted an inner tubular sheath which in turn houses a guide wire which is axially movable through the sheath. The medical device is mounted on the guide wire and can be collapsed within the sheath and body for deployment. An outer distal end of the sheath is provided with circumferentially spaced-apart axial slits extending proximally from the distal end of the sheath which sub-divide the distal end of the tubular side wall of the sheath into a number of complementary tube sections which are movable apart when the sheath is pushed out of the distal end of the body to engage or deploy the medical device.

19 Claims, 6 Drawing Sheets

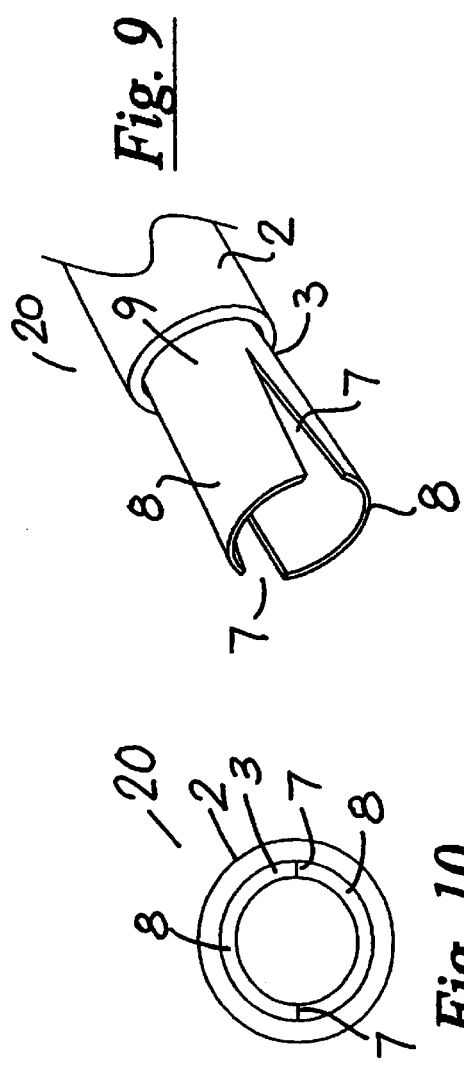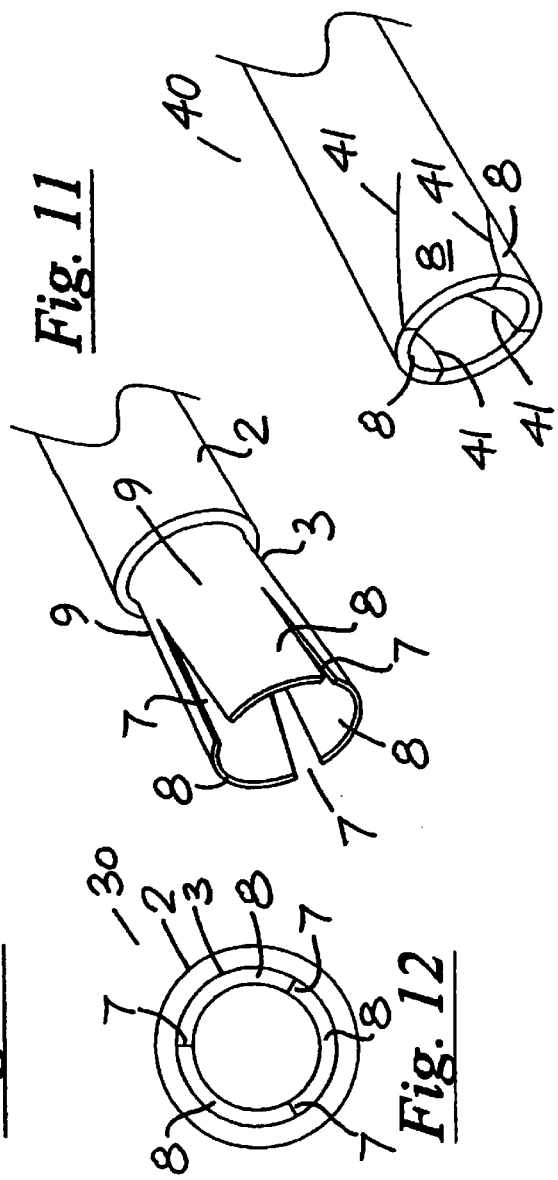

DELIVERY CATHETER

This is a Continuation of Application No. PCT/IE99/00020, filed Apr. 1, 1999.

FIELD OF THE INVENTION

The present invention relates to a catheter for delivery of implant devices of the general type comprising a loading means for enveloping the implant within a catheter tube and a releasable implant gripping means.

BACKGROUND OF THE INVENTION

There are many forms of medical implant devices, deployed transvascularly by means of a catheter, which are used where there is a requirement to occlude a vessel, fill a void or plug a defect in the treatment of medical conditions, whether they be acute or chronic situations or cosmetic situations.

These medical implant devices are delivered either transarterially or transvenously. The medical implant device is loaded in a folded or collapsed position within a tip of a catheter. The tip of the catheter is directed to the defect which is to be repaired and then the medical implant device is delivered from the catheter. Once out of the catheter the medical implant device is expanded to its full size to occlude the defect. Many of the known medical implant devices used are unsuitable for some applications because of their size and rigidity and we have proposed in certain co-pending patent applications the provision of a replacement technology for conventionally used coils, wire frame occlusion devices and the like. These improved implant devices have included the provision of highly compressible implant devices such as those having a compressible porous polymeric structure. One of the problems, however, with compressible devices and indeed many other devices is that they often do not react favourably to the conventional way of loading them in the catheter, which comprises pushing or pulling the implant into an end of the catheter. Very often by their very nature which allows them expand and assume the correct shape within the void this is the very construction that makes them difficult to push and manipulate. This also applies to other types of devices as well as implants having a compressible porous polymeric structure. Indeed what is required with most of these implants which can be loosely described as being expandable is that they be correctly compressed within the catheter. It is also desirable that if the implant device is initially deployed incorrectly or in the wrong location that the implant device can be easily loaded again in a collapsed position within the catheter for redeployment.

U.S. Pat. No. 5,683,451 discloses apparatus and a method for endoluminal placement of intraluminal tubular prostheses such as grafts and stents. The devices are collapsed within a distal end of a delivery catheter by a set of spaced-apart hard elongate runners mounted at a distal end of an inner catheter slidable within the delivery catheter.

WO 98/14224 discloses apparatus and a method for retrieving partially deployed balloon expandable stents from within a vein or artery. The apparatus has a grasping device comprising either an expandable tube or a plurality of spaced-apart nitinol fingers with elastomeric web stretched therebetween. The tube or fingers can be manipulated to open to grasp a stent and then closed to grip the stent for withdrawal into a catheter.

U.S. Pat. No. 5,026,277 discloses a device for the deployment or retraction of a self-expanding stent in a body canal. The device has a tubular outer sleeve and an inner core slidable within the sleeve, the stent being collapsed against the core and being held in the collapsed state between the core and the outer sleeve for deployment.

It is an object of the present invention to provide a catheter that has the ability to deliver devices that don't have axial stiffness.

SUMMARY OF THE INVENTION

According to the invention there is provided a catheter for transvascular deployment of a radially compressible medical device, comprising an elongate tubular outer body having a proximal end and a distal end, a tubular housing being formed at the distal end of the body for reception of the medical device in a collapsed state, a deployment means for engagement with the medical device being movable through the housing to move the medical device between a collapsed stored position within the housing and a deployment position externally of the housing, and loading means for radially collapsing the medical device for engagement within the housing, the loading means being movable relative to the body for engagement with the medical device, characterised in that the loading means comprises a tubular sheath having a proximal end and a distal end, the distal end of the sheath being slidably mounted within the distal end of the body, the distal end of the sheath having a tubular side wall with two or more slits in the side wall of the sheath extending proximally from a distal end of the sheath, the slits sub-dividing the tubular side wall of the distal end of the sheath into a number of complementary tube sections which are movable between a closed position defining a tubular housing for reception of the medical device and an open position to enlarge the distal end of the sheath when the distal end of the sheath is moved outwardly of the distal end of the body.

By using a tubular loading means which is movable relative to the medical device for its securement, it is possible to grip the medical device in whatever way one requires and thus ensure that, for example, with a compressible or distortable medical device it is not compressed in an undesired way. Further, as the loading device is tubular, it provides continuous support fully around the medical device ensuring an even compression of the medical device. This is particularly desirable with foam type medical devices which do not have a support frame and so are easily distorted. The tubular loading means allows controlled compression of such medical devices so that they will open in a desired manner upon deployment.

In a preferred embodiment the slits in the distal end of the sheath comprises two or more circumferentially spaced-apart axially extending slits in the distal end of the sheath.

In another embodiment the slits in the distal end of the sheath comprise two or more circumferentially spaced-apart helical slits in the distal end of the sheath.

In a further embodiment each tube section has an inner end hingedly connected to the sheath body by a hinge. Preferably each hinge is integrally formed with the sheath.

Conveniently each hinge may be biased to urge the tube section towards the open position.

In another embodiment a pair of slits are provided in the distal end of the sheath, sub-dividing the distal end of the sheath into two complementary tube sections hingedly connected at their inner ends to the sheath.

In a further embodiment three slits are provided in the distal end of the sheath, sub-dividing the distal end of the sheath into three complementary tube sections hingedly connected at their inner ends to the sheath.

In a further embodiment four slits are provided in the distal end of the sheath, sub-dividing the distal end of the sheath into four complementary tube sections hingedly connected at their inner ends to the sheath.

In another embodiment the deployment means for the medical device is a guidewire extending through the sheath.

Conveniently the catheter body is formed from a low friction material.

BRIEF DESCRIPTION OF THE DRAWINGS

The invention will be more clearly understood from the following description of some embodiments thereof given by way of example only with reference to the accompanying drawings in which:

FIG. 9 is a perspective view similar to FIG. 4 showing another catheter according to a second embodiment of the invention;

FIG. 10 is an end elevational view of the catheter of FIG. 9;

FIG. 11 is a perspective view similar to FIG. 4 showing a further catheter according to a third embodiment of the invention;

FIG. 12 is an end elevational view of the catheter of FIG. 11; and

FIG. 13 is a detail perspective view of a split sheath forming portion of another catheter of the invention.

DESCRIPTION OF THE PREFERRED EMBODIMENT

Figure 1:
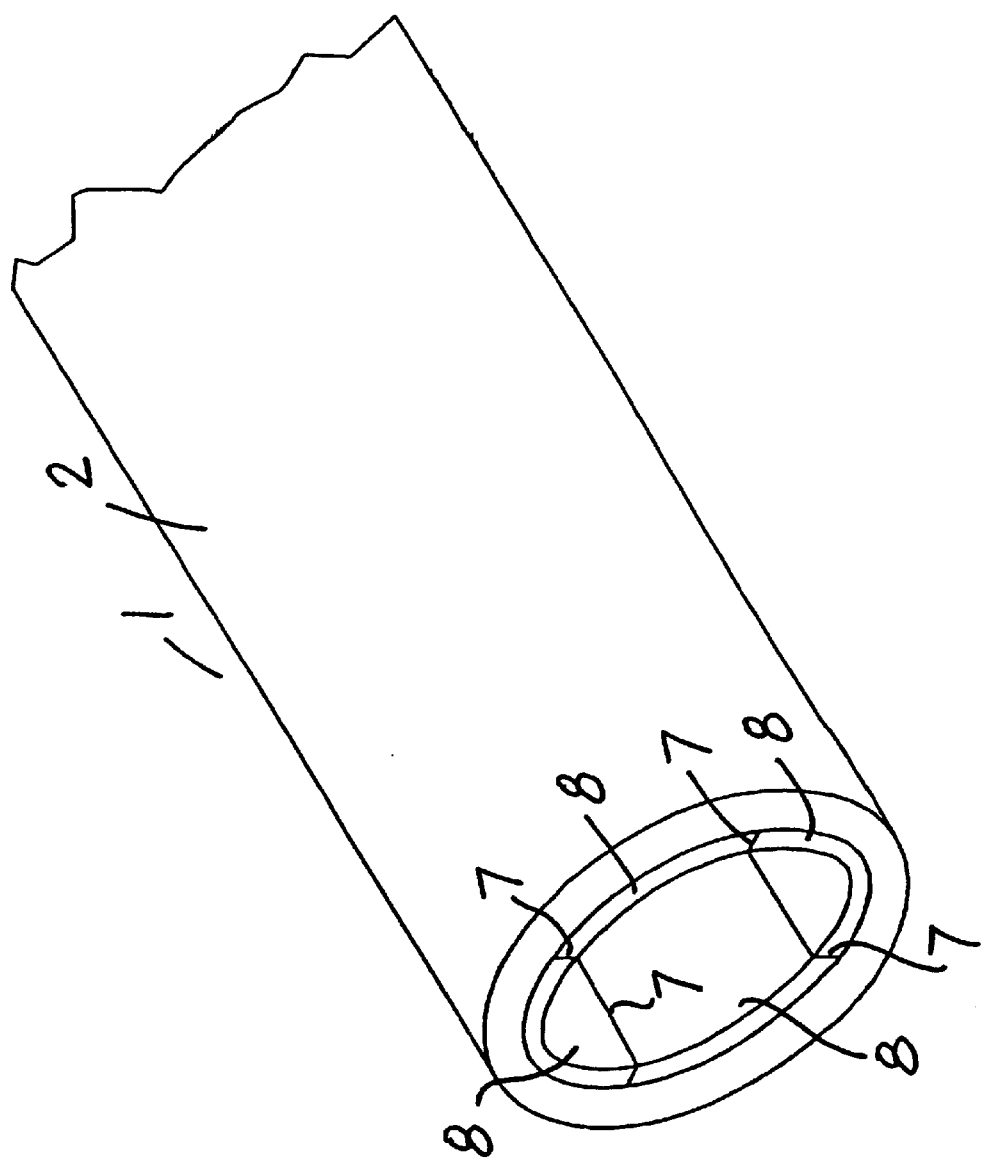
FIG. 1 is a perspective view of a distal end of a catheter according to the invention.
Figure 2:
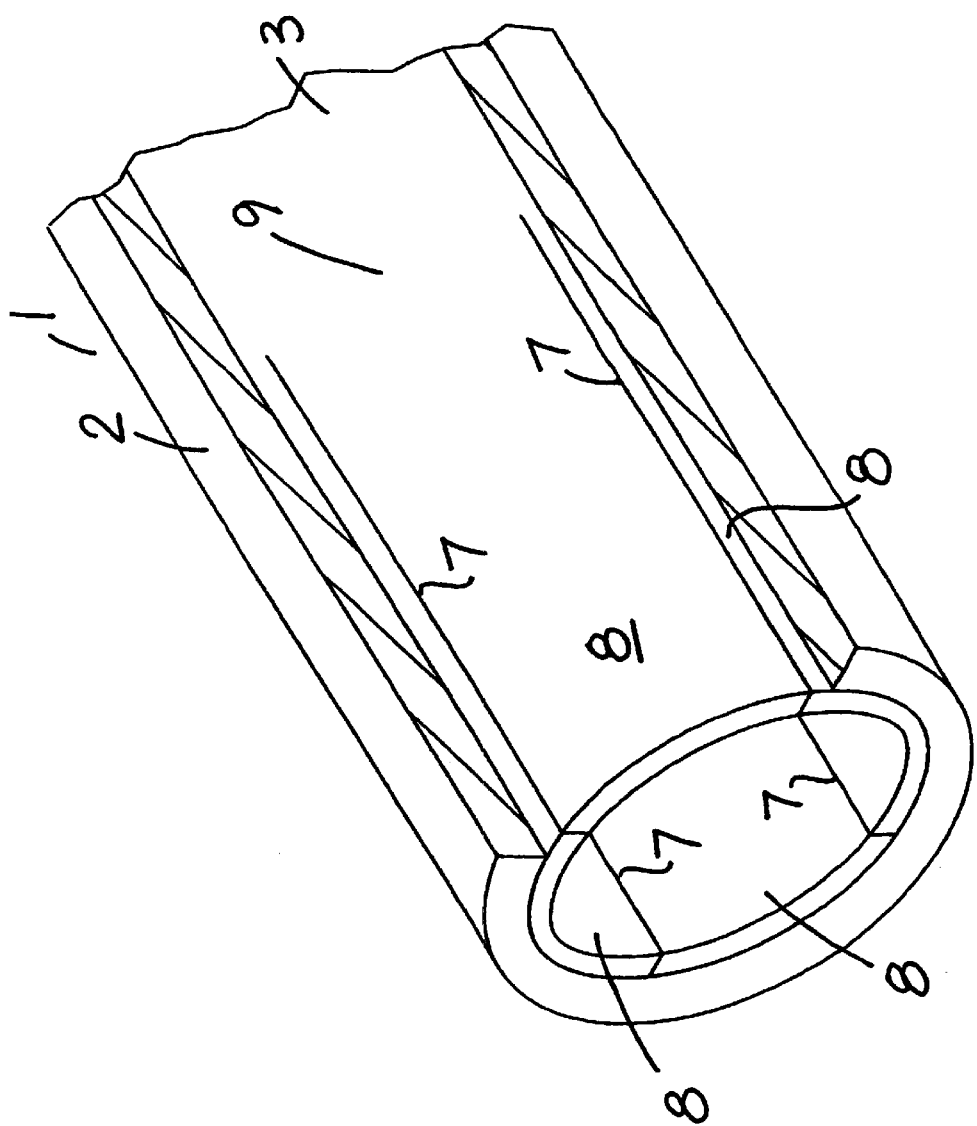
FIG. 2 is a partially cut-away perspective view of the distal end of the catheter.
Figure 3:
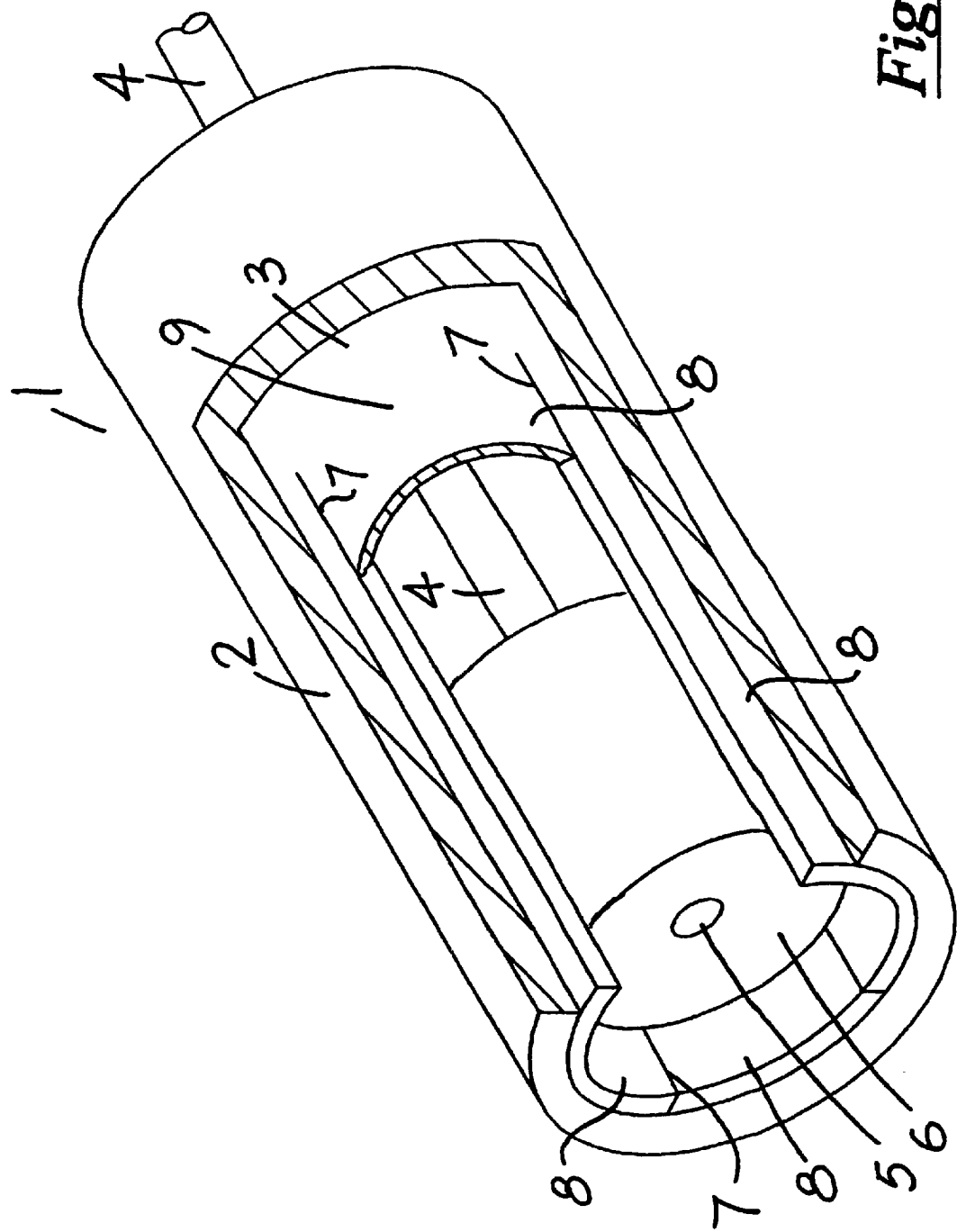
FIG. 3 is a view similar to FIG. 2 showing a compressible medical implant device loaded in the catheter for deployment.
Figure 4:
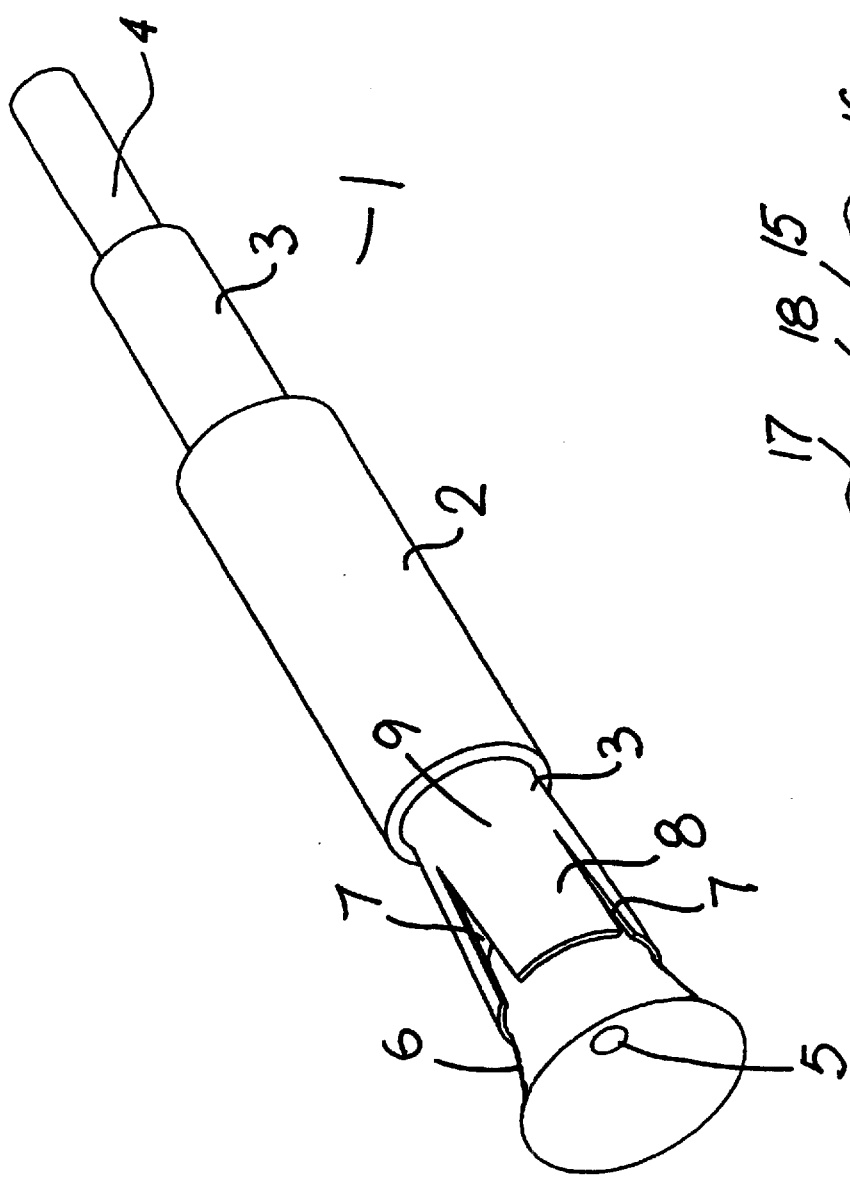
FIG. 4 is a perspective view of the distal end of the catheter according to the invention.

Referring to the drawings, and initially to FIGS. 1 to 5 thereof, there is illustrated a catheter according to the invention indicated generally by the reference numeral 1 and comprising an outer catheter tube 2 within which is slidably mounted an inner tubular sheath 3 which in turn houses a guide wire 4 which is slidable within the inner tubular sheath 3. At an outer end of the guide wire 4 is a gripper 5 of any suitable construction engaging a medical implant device 6 of compressible foam or other porous material. An outer end of the inner tubular sheath 3 is provided with four circumferentially spaced apart and axially arranged slits 7 which sub-divide the tubular side wall at the outer distal end of the inner tubular sheath 3 into four tube sections 8.

Each of the tube sections 8 is attached by a hinge joint 9 at an inner end of the tube section 8 to the inner support tube 3. Thus, each tube section 8 will pivot about the hinge joint 9 for movement between a closed position (FIG. 6) defining a tubular housing for reception of the medical implant device 6 and an open position (FIGS. 4 and 8) to enlarge the distal end of the inner tubular sheath 3 when the distal end of the inner tubular sheath 3 is moved outwardly of the catheter 2 for reception or deployment of the medical implant device 6. It will be noted from FIG. 6 that when the medical device 6 is mounted within the inner tubular sheath 3 which is in a closed position retained within the distal end of the catheter 2, the medical implant device 6 is evenly compressed into a cylindrical configuration.

Figure 5:
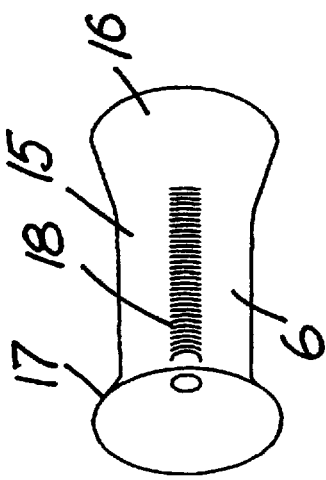
FIG. 5 is an enlarged perspective view of a medical implant device for use with the catheter.

The implant device 6 illustrated in the drawings is shown in more detail in FIG. 5. The implant device 6 comprises a body 15 of a compressible porous plastics material of open-cell structure such as a plastic foam. Each end 16, 17 of the body 15 is flared outwardly in a trumpet shape. The foam body 15 is moulded about a platinum spring core 18 forming portion of the gripper 5 for attachment to the wire 4. It will be appreciated that this particular implant is chosen for illustration purposes only and the catheter of the invention is suitable for deploying many other types of compressible implant devices.

Figure 6:
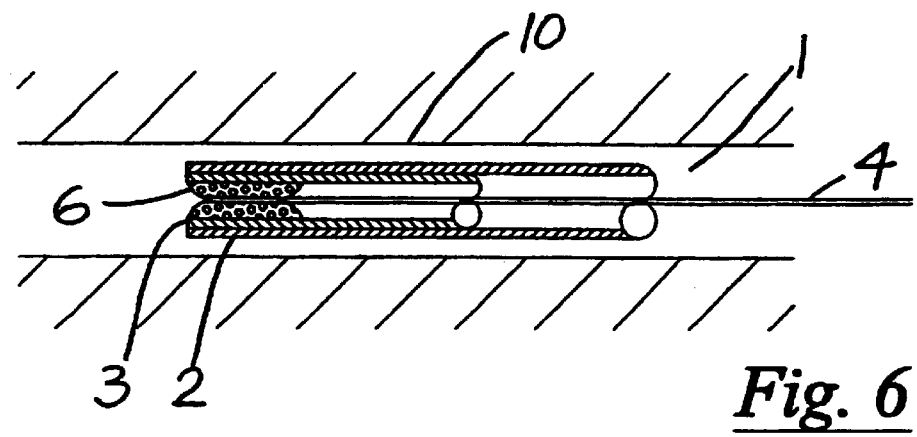
FIG. 6 is a sectional view showing the catheter in use in a first stage of deploying the implant device.
Figure 7:
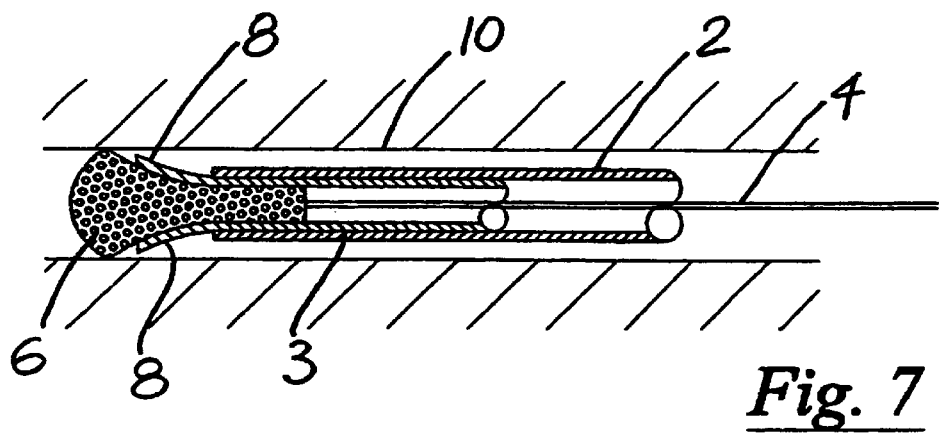
FIG. 7 is a view similar to FIG. 6 showing a second stage of the deployment of the implant device.
Figure 8:
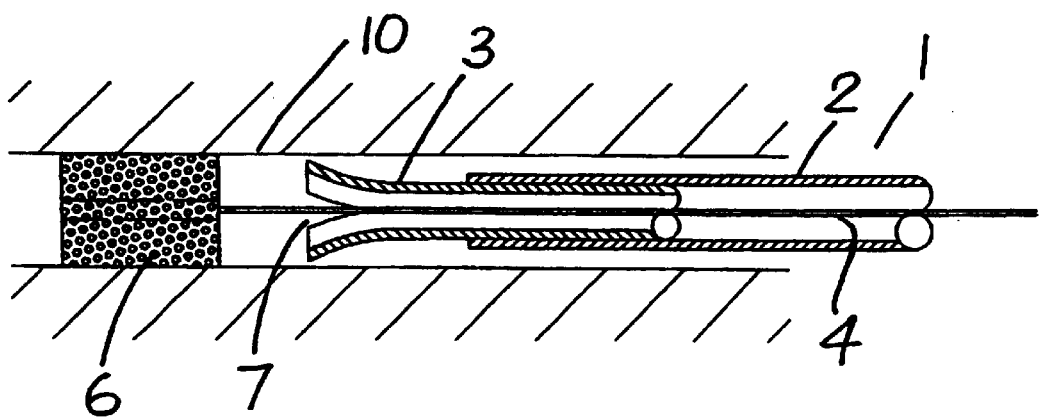
FIG. 8 is a view similar to FIG. 6 showing a third stage in the deployment of the implant device.

In use, to load the implant device 6 in the catheter 1 the gripper 5 at the end of the wire 4 is connected to the implant 6. The inner tubular sheath 3 is then pushed out of the other catheter tube 2. As it is pushed out, the tube sections 8 will splay apart effectively creating a funnel. Upon withdrawal of the wire 4 the implant device 6 is withdrawn into the funnel thus created. Then the outer catheter tube 2 is advanced to capture the protruding end of the inner tubular sheath 3 which collapses the implant 6 radially in a controlled manner. The implant device 6 is now housed within the outer catheter tube 2 in a collapsed position as shown in FIG. 6. The catheter 1 is then delivered transarterially or transvenously as required until an outer end of the catheter 1 is delivered to a desired location within a vessel 10 as illustrated in FIG. 6. The outer catheter tube 2 is then withdrawn whilst holding the wire 4 and inner tubular sheath 3 steady. Next the inner tubular sheath 3 is partially withdrawn, as shown in FIG. 7, to establish a distal end of the implant device within the vessel 10. As the inner tubular sheath 3 retracts the implant device 6 is free to expand to engage the vessel walls. If the physician is satisfied that the distal end of the implant device 6 is incorrectly positioned within the vessel 10, the inner tubular sheath 3 is retracted further to release the proximal portion of the implant device which freely expands into the vessel 10 as shown in FIG. 8.

It will be appreciated that if by any chance the implant device 6 is not correctly positioned, that it can be readily re-loaded in the catheter 1 and then correctly manipulated again into position in the opening and deployed as previously described. For example, the particular implant illustrated in the drawings would tend to crumple if loaded, as is conventionally the case, when pushing in and out of the catheter tube. It will be appreciated that it is better to radially compress the implant than to pull or manipulate it axially. This is achieved by the inner tubular sheath 3 of the catheter 1 which radially compresses the implant device 6 as it is withdrawn into the outer catheter tube 2.

Referring now to FIGS. 9 and 10, there is shown another catheter according to the invention indicated generally by the reference numeral 20. Parts similar to those described previously are assigned the same reference numerals. In this case, two slits 7 are provided at the distal end of the inner tubular sheath 3. Operation of the catheter 20 is similar to that described previously for the catheter of FIGS. 1 to 8.

Referring now to FIGS. 11 and 12, there is illustrated another catheter according to a third embodiment of the invention, indicated generally by the reference numeral 30. Parts similar to those described previously are assigned the same reference numerals. In this case, three slits 7 are provided at the distal end of the inner tubular sheath 3. Operation of the catheter 30 is similar to that described previously for the catheter of FIGS. 1 to 8.

It will also be appreciated that any number of slits are possible at the outer end of the inner tubular sheath 3, however, ideally there should be at least two. Also different arrangements of the orientation and positioning of the slits at the distal end of the sheath are possible. Instead of extending axially as described above the slits may extend helically along the sheath. Helical arrangement is shown in FIG. 13 which shows a sheath 40 with helical slits 41.

It is envisaged that various forms of implant device may be used and that further the inner tubular sheath 3 and the outer catheter tube 2 may be manufactured from any suitable plastics material, or indeed any other flexible material.

The invention is not limited to the embodiments hereinbefore described which may be varied in both construction and detail within the scope of the appended claims.

What is claimed is:

1. A catheter for transvascular development of a radially compressible medical device, comprising an elongate tubular outer body having a proximal end and a distal end, a tubular housing portion formed at the distal end of the body for reception of the medical device in a collapsed state, a deployment means for engagement with the medical device being movable through the housing portion to move the medical device between a collapsed stored position within the housing portion and a deployment position externally of the housing portion, and loading means for radially collapsing the medical device for engagement within the housing portion, the loading means being movable relative to the body for engagement with the medical device, the loading means comprises a tubular sheath having a proximal end and a distal end, the distal end of the sheath being slidably mounted within the distal end of the body, the distal end of the sheath having a tubular side wall with two or more circumferentially spaced apart helical slits in the side wall of the sheath extending proximally from a distal end of the sheath, the slits sub-dividing the tubular side wall of the distal end of the sheath into a number of complementary tube sections which are movable between a closed position defining a tubular housing for reception of the medical device and an open position to enlarge the distal end of the sheath when the distal end of the sheath is moved outwardly of the distal end of the body.

2. A catheter as claimed in claim 1, wherein each tube section has a proximal end hingedly connected to the sheath body by a hinge.

3. A catheter as claimed in claim 2, wherein each hinge is integrally formed with the sheath.

4. A catheter as claimed in claim 2 wherein each hinge is biased to urge the tube section towards the open position.

5. A catheter as claimed in claim 1, wherein a pair of slits are provided in the distal end of the sheath, sub-dividing the distal end of the sheath into two complementary tube sections hingedly connected at their proximal ends to a body portion of the sheath.

6. A catheter as claimed in claim 1, wherein three slits are provided in the distal end of the sheath, sub-dividing the distal end of the sheath into three complementary tube sections hingedly connected at their proximal ends to a body portion of the sheath.

7. A catheter as claimed in claim 1, wherein four slits are provided in the distal end of the sheath, sub-dividing the distal end of the sheath into four complementary tube sections hingedly connected at their proximal ends to a body portion of the sheath.

8. A catheter as claimed in claim 1, wherein the deployment means for the medical device is a guidewire extending through the sheath.

9. A catheter as claimed in claim 1 in which the catheter body is formed from a low friction material.

10. A catheter as claimed in claim 1, wherein the medical device includes a medical implant.

11. A catheter for transvascular development of a radially compressible medical device, comprising an elongate tubular body having a proximal end and a distal end, a tubular housing portion formed at the distal end of the body for reception of the medical device in a collapsed state;

a deployment device adapted to engage the medical device being movable through the housing portion to move the medical device between a collapsed stored position within the housing portion and a deployment position externally of the housing portion; and a tubular sheath adapted to assist in radially collapsing the medical device for engagement within the housing, the tubular sheath being movable relative to the body for engagement with the medical device, and comprising a proximal end and a distal end, the distal end of the tubular sheath being slidably mounted within the distal end of the body, the distal end of the tubular sheath having a tubular side wall with two or more helical slits extending proximally from a distal end of the tubular sheath, and the slits sub-dividing the tubular side wall of the distal end of the tubular sheath into a number of tube sections which are movable between a closed position defining a tubular housing for reception of the medical device and an open position to enlarge the distal end of the tubular sheath when the distal end of the tubular sheath is moved outwardly of the distal end of the body.

12. A catheter as claimed in claim 11, wherein each tube section has an proximal end hingedly connected to a body portion of the tubular sheath.

13. A catheter as claimed in claim 11 wherein each tube section is biased towards the open position.

14. A catheter as claimed in claim 11 wherein a pair of slits are provided in the distal end of the sheath, sub-dividing the distal end of the sheath into two complementary tube sections hingedly connected at their proximal ends to a body portion of the tubular sheath.

15. A catheter as claimed in claim 11, wherein three slits are provided in the distal end of the sheath, sub-dividing the distal end of the sheath into three complementary tube sections hingedly connected at their proximal ends to a body portion of the tubular sheath.

16. A catheter as claimed in claim 11, wherein four slits are provided in the distal end of the sheath, sub-dividing the distal end of the sheath into four complementary tube sections hingedly connected at their proximal ends to a body portion of the tubular sheath.

17. A catheter as claimed in claim 11, wherein the deployment device is a guidewide extending through the tubular sheath.

18. A catheter as claimed in claim 11, wherein the catheter body is formed from a low friction material.

19. A catheter as claimed in claim 11, wherein the medical device includes a medical implant.

* * * * *

UNITED STATES PATENT AND TRADEMARK OFFICE
CERTIFICATE OF CORRECTION

PATENT NO.    : 6,514,280 B1
DATED         : February 4, 2003
INVENTOR(S)   : Paul Gilson It is certified that error appears in the above-identified patent and that said Letters Patent is hereby corrected as shown below:

Column 6,
Line 16, replace "device being" with -- device and being --.

Signed and Sealed this

Twenty-fifth Day of March, 2003

JAMES E. ROGAN
*Director of the United States Patent and Trademark Office*